US011266366B2

(12) United States Patent
Daugirdas et al.

(10) Patent No.: US 11,266,366 B2
(45) Date of Patent: Mar. 8, 2022

(54) METHODS AND SYSTEMS FOR C-ARM CABLE MANAGEMENT

(71) Applicant: GE Precision Healthcare LLC, Milwaukee, WI (US)

(72) Inventors: Kristofer Daugirdas, Salt Lake City, UT (US); David Barker, Salt Lake City, UT (US); Nathan Pack, South Jordan, UT (US); Alina Tran, Taylorsville, UT (US)

(73) Assignee: GE Precision Healthcare LLC, Milwaukee, WI (US)

( * ) Notice: Subject to any disclaimer, the term of this patent is extended or adjusted under 35 U.S.C. 154(b) by 90 days.

(21) Appl. No.: 16/690,095

(22) Filed: Nov. 20, 2019

(65) Prior Publication Data

US 2021/0145384 A1 May 20, 2021

(51) Int. Cl.
*A61B 6/00* (2006.01)
*H05G 1/02* (2006.01)
*H01R 35/04* (2006.01)

(52) U.S. Cl.
CPC .............. *A61B 6/4441* (2013.01); *A61B 6/56* (2013.01); *H01R 35/04* (2013.01); *H05G 1/02* (2013.01)

(58) Field of Classification Search
CPC .......... A61B 6/4441; A61B 6/56; H05G 1/32; H01R 35/04
See application file for complete search history.

(56) References Cited

U.S. PATENT DOCUMENTS

| 4,288,700 A * | 9/1981 | Grass ................... A61B 6/4441 174/86 |
| 4,705,243 A * | 11/1987 | Hartmann ............ B23K 11/362 248/160 |
| 5,436,461 A * | 7/1995 | Saffer .................. A61B 6/4441 250/522.1 |
| 5,450,466 A * | 9/1995 | Kadowaki ............ A61B 6/4405 378/189 |
| 5,483,957 A * | 1/1996 | Janssen ..................... A61B 6/56 378/194 |
| 5,912,943 A * | 6/1999 | Deucher .................. H05G 1/02 378/98.8 |
| 6,234,671 B1 * | 5/2001 | Solomon ............... A61B 6/4441 250/492.3 |
| 9,144,145 B2 | 9/2015 | Fürst et al. |
| 9,204,851 B2 | 12/2015 | Baumann et al. |
| 9,481,095 B2 * | 11/2016 | Takahashi ............ B25J 19/0025 |
| 2002/0174515 A1 | 11/2002 | Strong |
| 2003/0211766 A1 * | 11/2003 | Krug ...................... H01R 35/04 439/165 |

(Continued)

*Primary Examiner* — Dani Fox
*Assistant Examiner* — Soorena Kefayati

(57) ABSTRACT

Various methods and systems are provided for C-arm cable management. In one embodiment, an assembly for a C-arm imaging system comprises a cable guide configured to rotate around a rotational axis arranged at an angle to a surface of a C-shaped portion of the C-arm imaging system to which the assembly mounts, with the cable guide including a rigid elongate portion extending outward from the rotational axis and configured to enclose a portion of a cable of the C-arm imaging system. In this way, the cable guide may maintain the cable of the C-arm imaging system outside of a sterile imaging area of the C-arm imaging system.

17 Claims, 5 Drawing Sheets

(56) References Cited

U.S. PATENT DOCUMENTS

| | | | | |
|---|---|---|---|---|
| 2007/0280426 A1* | 12/2007 | Saffer | A61B 6/4441 | 378/198 |
| 2009/0074149 A1* | 3/2009 | Van Der Ende | A61B 6/4441 | 378/197 |
| 2011/0072931 A1* | 3/2011 | Gro | H02G 11/02 | 74/490.02 |
| 2012/0085078 A1* | 4/2012 | Rijken | H02G 3/0475 | 59/78.1 |
| 2012/0121071 A1* | 5/2012 | Herrmann | A61B 6/56 | 378/194 |
| 2012/0275571 A1* | 11/2012 | Neuber | A61B 6/56 | 378/194 |
| 2014/0033851 A1* | 2/2014 | Hermey | B25J 19/00 | 74/490.02 |
| 2014/0037058 A1* | 2/2014 | Allen | A61B 6/4441 | 378/62 |
| 2015/0136127 A1* | 5/2015 | Dimatteo | A61M 16/06 | 128/202.27 |
| 2015/0319831 A1* | 11/2015 | Fehre | A61B 6/4441 | 378/62 |
| 2015/0335387 A1* | 11/2015 | Atzinger | B25J 19/0025 | 606/130 |
| 2016/0322793 A1* | 11/2016 | Cuppen | H02G 3/32 | |
| 2017/0020468 A1* | 1/2017 | Bouvier | A61B 6/10 | |
| 2017/0023154 A1* | 1/2017 | Jaeker | B25J 19/0029 | |
| 2017/0215825 A1* | 8/2017 | Johnson | A61B 6/4441 | |
| 2017/0215826 A1* | 8/2017 | Johnson | A61B 6/547 | |
| 2017/0231585 A1* | 8/2017 | Atzinger | F16M 11/105 | 378/194 |
| 2017/0280541 A1* | 9/2017 | Limmer | B65H 75/4449 | |
| 2018/0333115 A1* | 11/2018 | Kraemer | A61B 6/4405 | |
| 2019/0029620 A1* | 1/2019 | Baumann | B25J 18/00 | |
| 2019/0089109 A1* | 3/2019 | Hirai | H01R 35/025 | |
| 2019/0099143 A1* | 4/2019 | Liu | A61B 6/447 | |

* cited by examiner

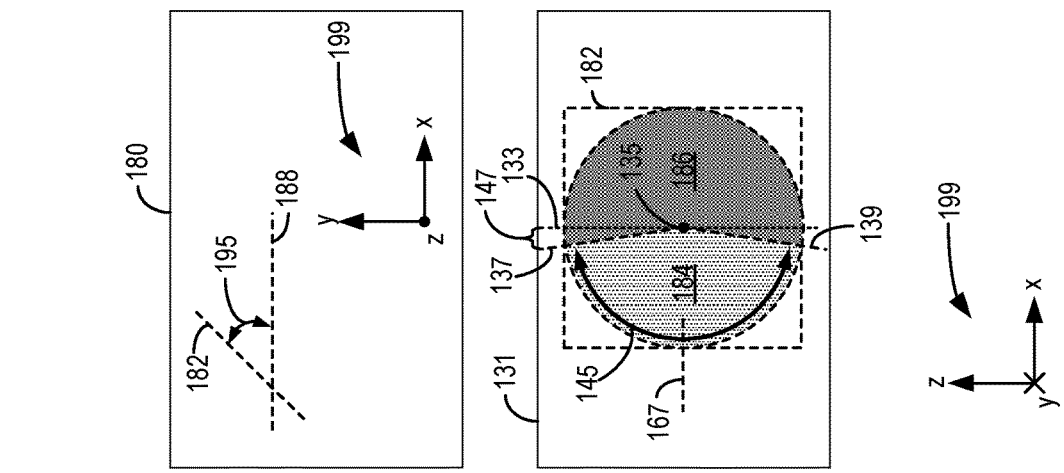
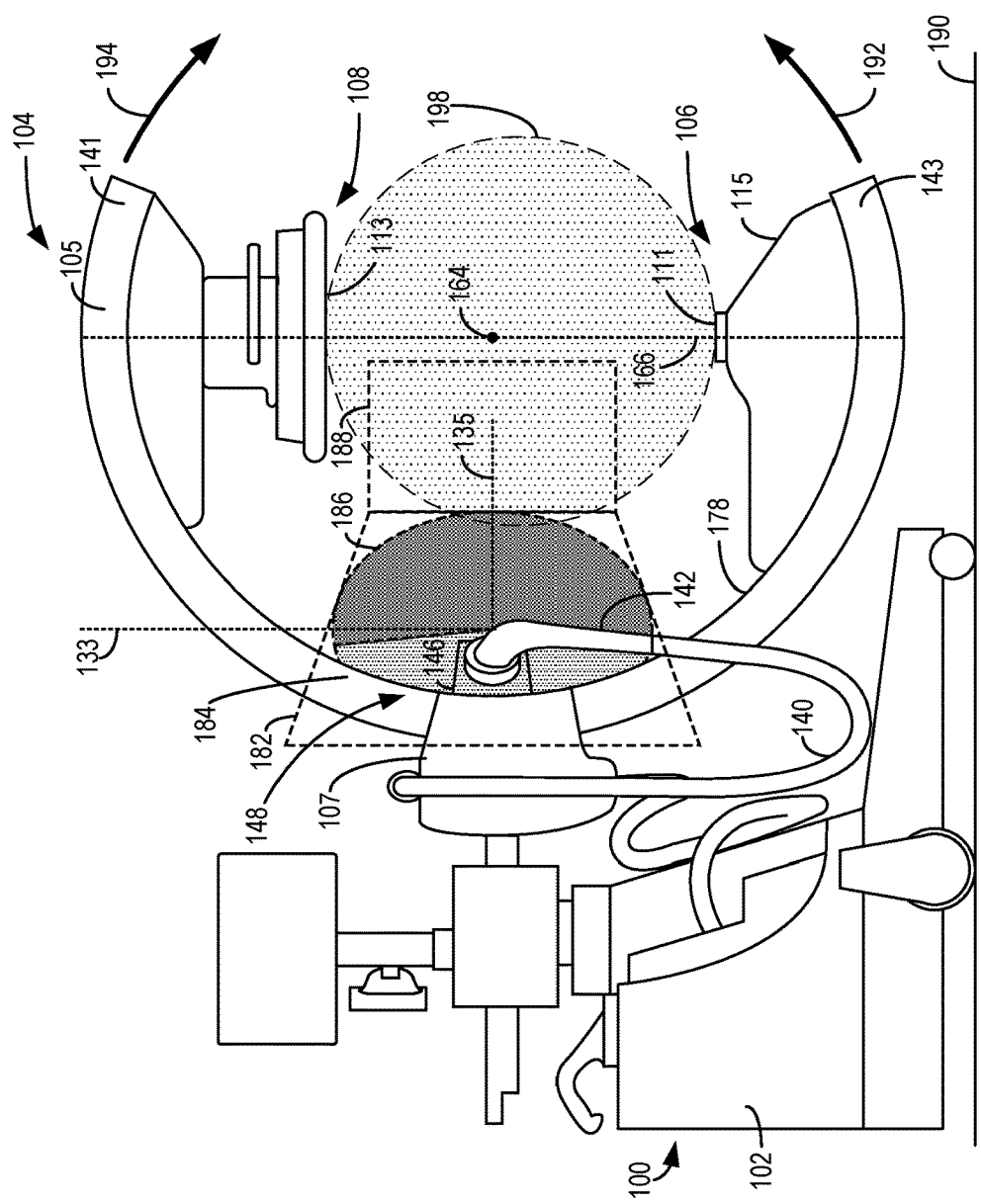
FIG. 1

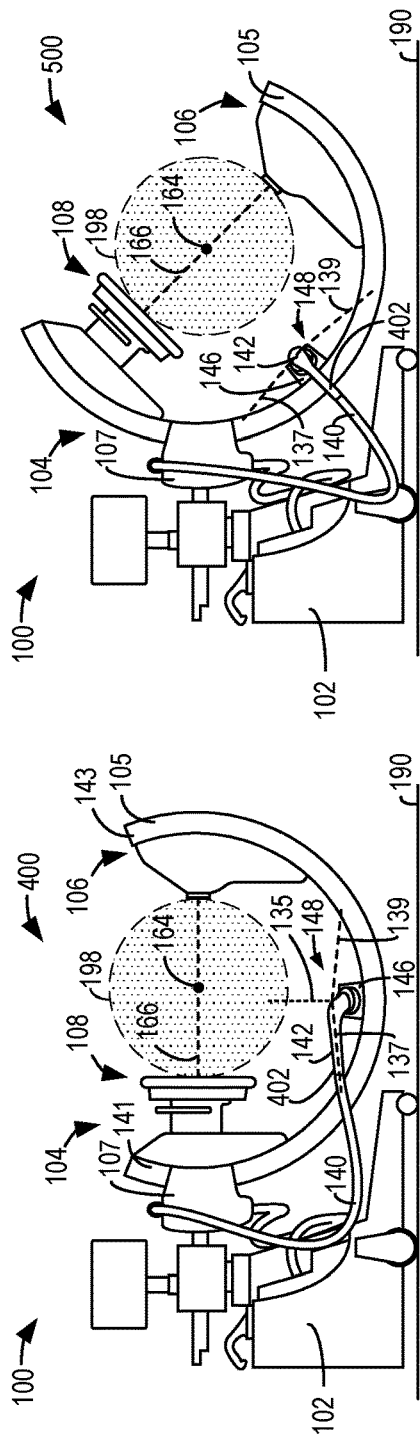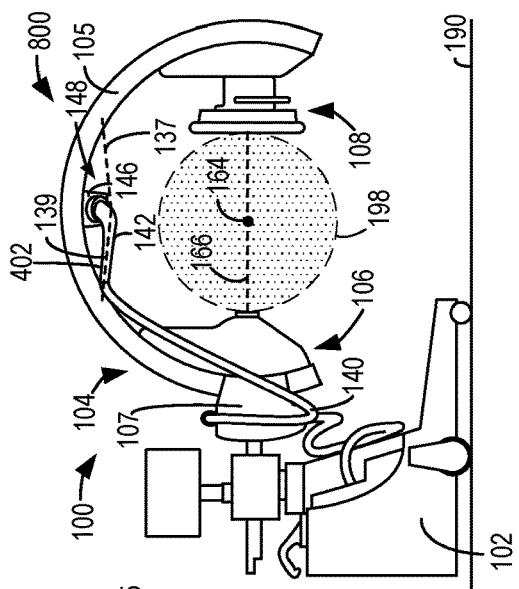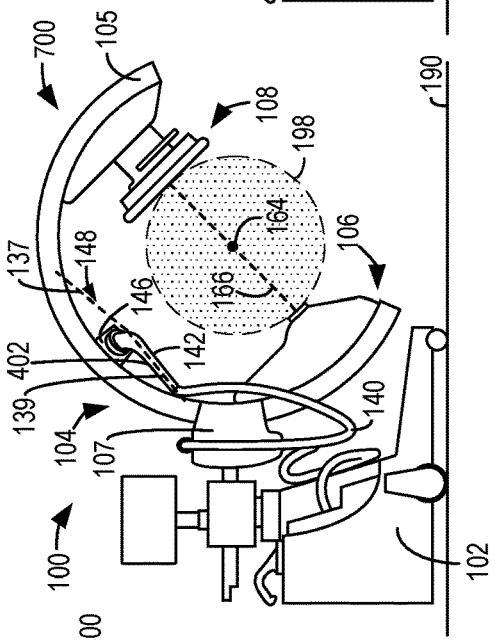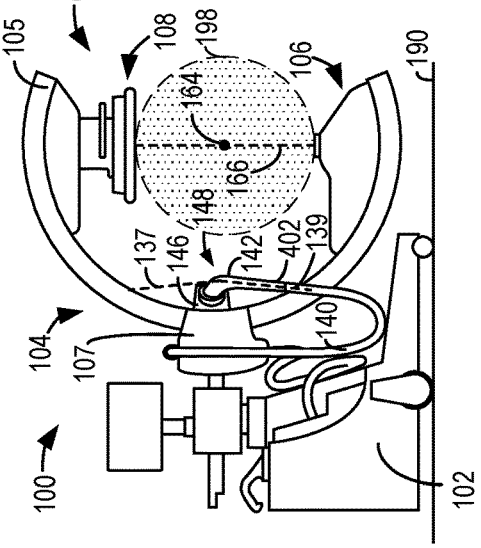

METHODS AND SYSTEMS FOR C-ARM CABLE MANAGEMENT

FIELD

Embodiments of the subject matter disclosed herein relate to medical imaging systems, and more particularly, to radiographic imaging systems.

BACKGROUND

Radiographic imaging systems may be used in various applications, including medical and industrial applications. In a medical environment, a radiographic imaging device may provide a non-invasive means of imaging tissue and bone of a patient. The imaging device may have the capability of capturing multiple images at designated intervals and displaying the images in a sequence to create a single image of the object being examined.

The imaging device may comprise a C-arm coupled to a base unit. The C-arm may include an x-ray source positioned at one end of the arm and a detector positioned at another end of the arm. A clearance may be provided between the x-ray source and the detector to receive an object, such as a portion of the patient's body, which may be irradiated with radiation from the x-ray source. Upon irradiating the object, the x-ray radiation penetrates through the object and is captured by the detector. By penetrating the object placed between the source and detector, the x-rays enable an image of the object to be captured and relayed to the display monitor, where the image may be displayed or stored and retrieved later.

BRIEF DESCRIPTION

In one embodiment, an assembly for a C-arm imaging system comprises a cable guide configured to rotate around a rotational axis arranged at an angle to a surface of a C-shaped portion of the C-arm imaging system to which the assembly mounts, with the cable guide including a rigid elongate portion extending outward from the rotational axis and configured to enclose a portion of a cable of the C-arm imaging system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 1 shows an imaging system including a C-arm and a cable swivel assembly.

FIGS. 4-8 show different rotational positions of the cable swivel assembly of the imaging system of FIG. 1 for different rotational positions of the C-arm.

DETAILED DESCRIPTION

Figure 2:
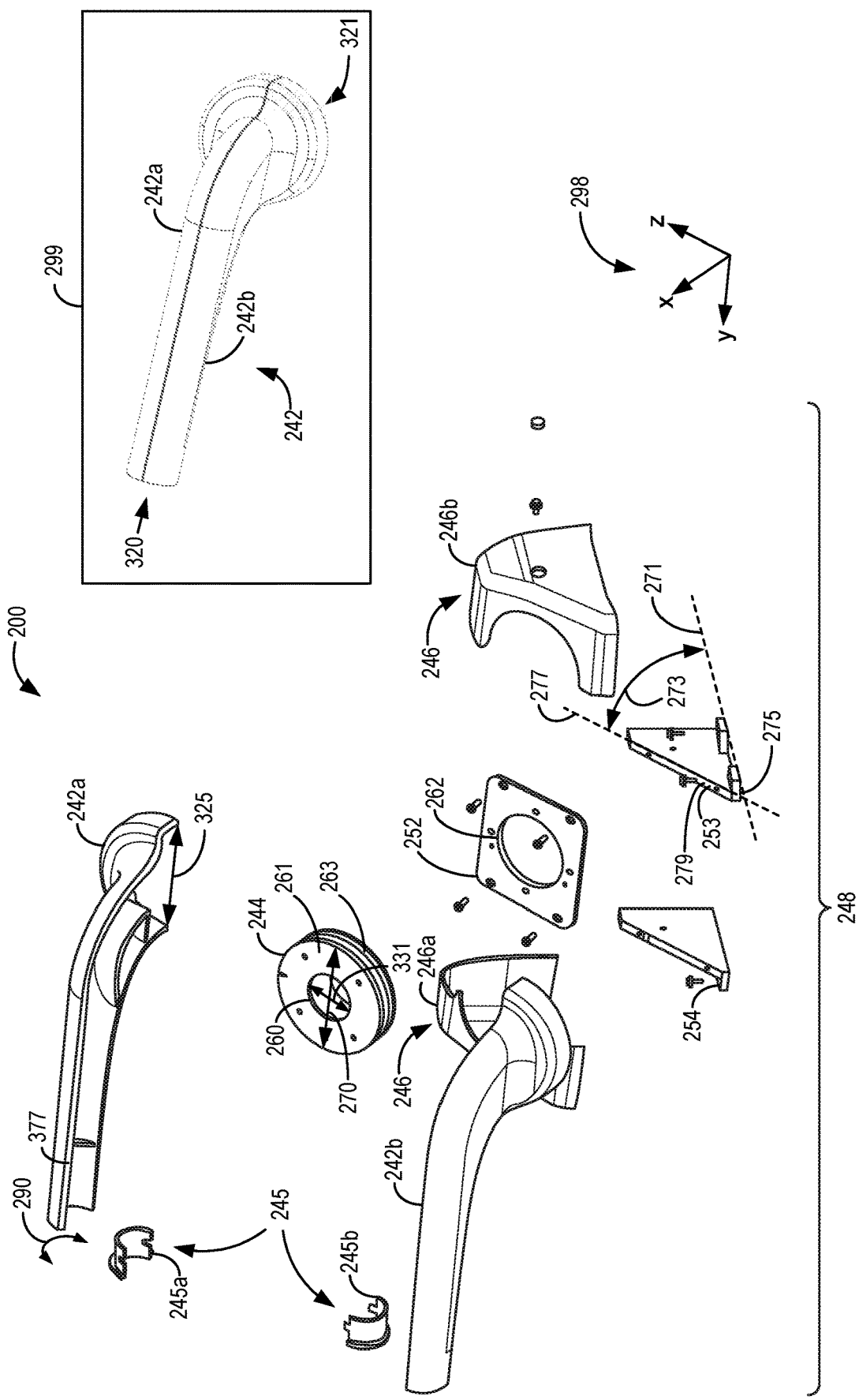
FIG. 2 shows an exploded view of a cable swivel assembly of an imaging system including a C-arm.
Figure 3:
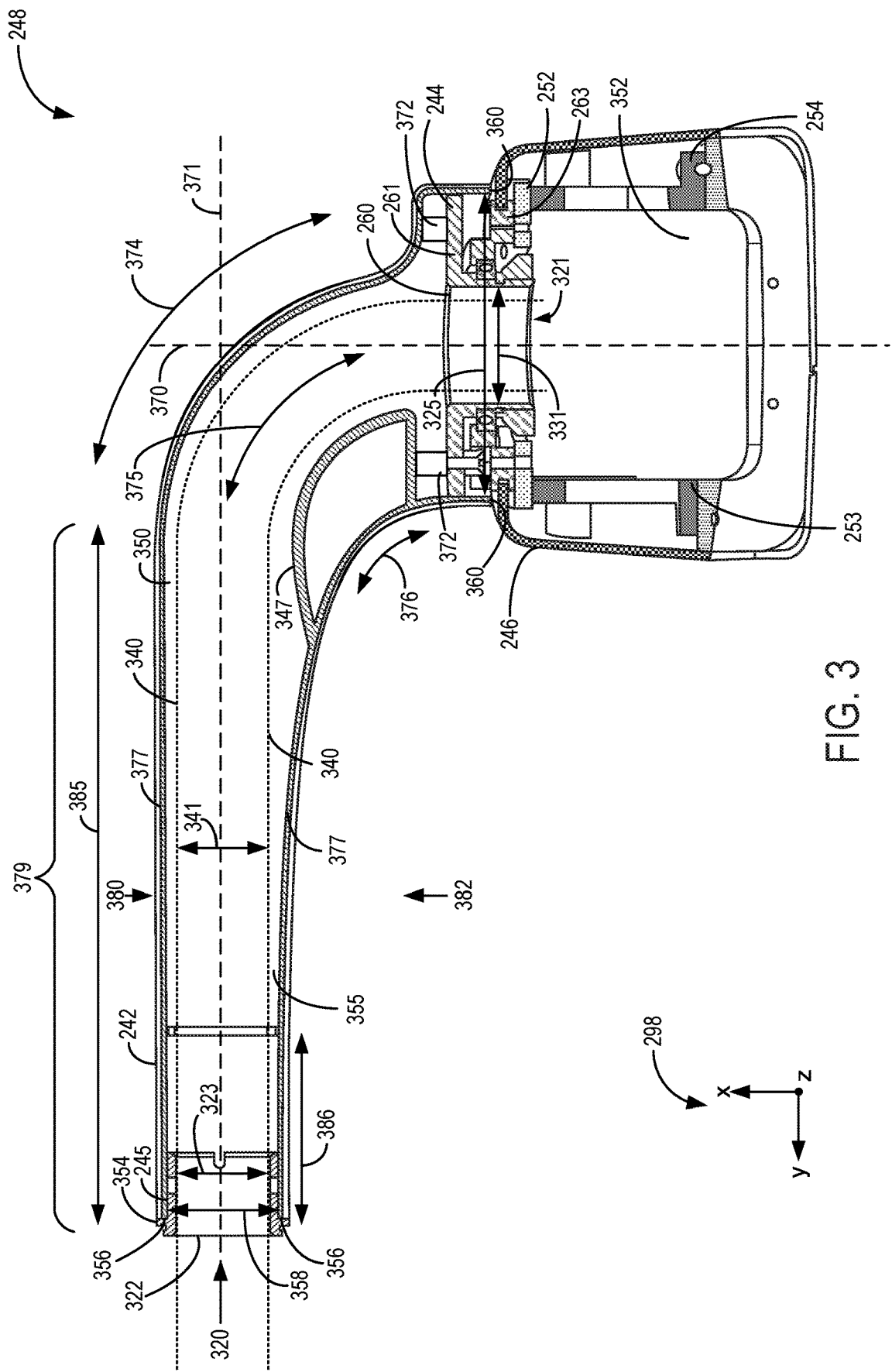
FIG. 3 shows a cross-sectional view of the cable swivel assembly of FIG. 2 in an assembled configuration.
Figure 9:
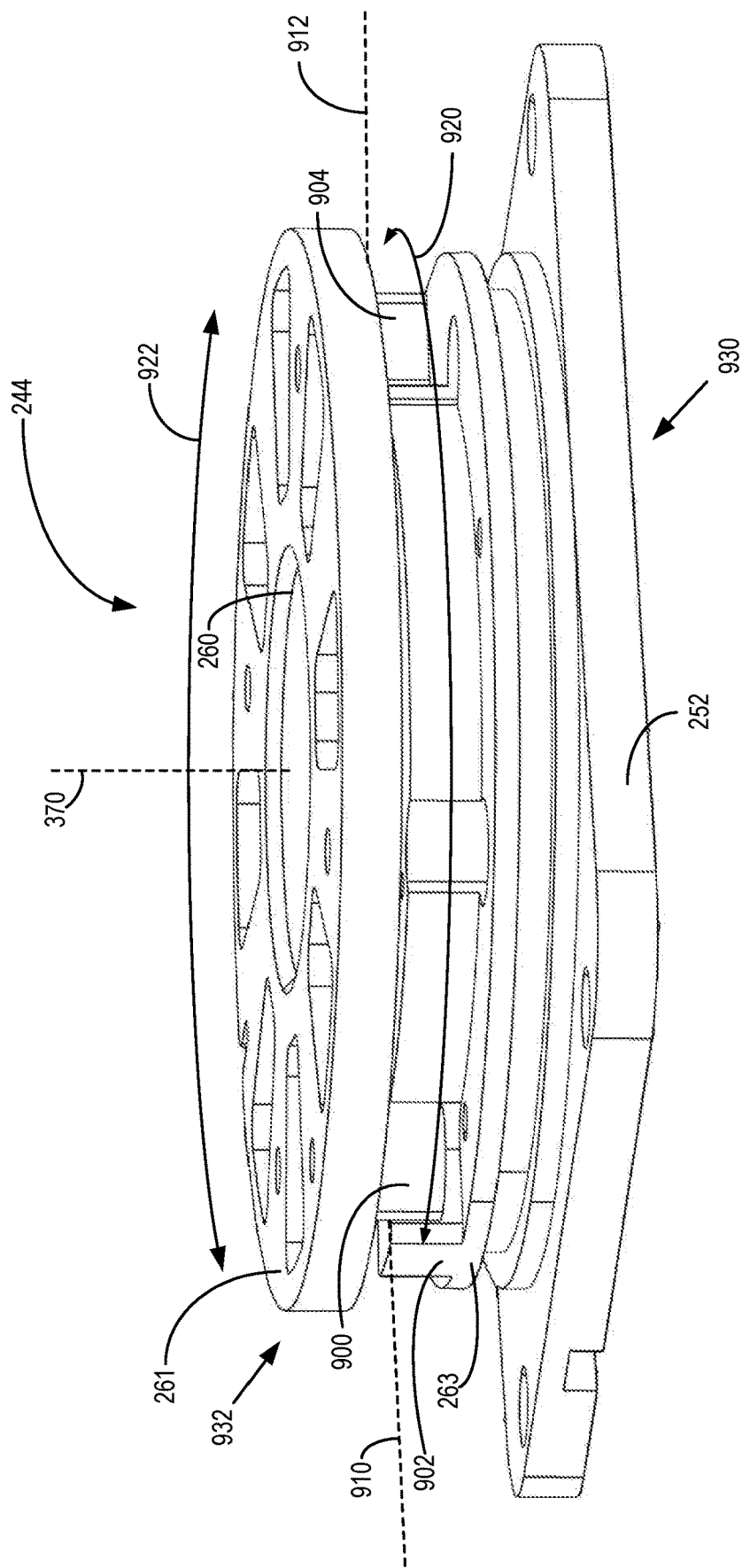
FIG. 9 shows a perspective view of a bearing and mounting plate of the cable swivel assembly of FIGS. 2-3.

The following description relates to various embodiments for an imaging system including a C-arm and a cable swivel assembly. An imaging system including a C-arm, such as the imaging system shown by FIG. 1, includes a cable swivel assembly configured to guide a position of a cable of the imaging system. The cable swivel assembly may be coupled to a C-shaped portion of the C-arm via a mounting plate arranged at an angle relative to a rotational plane of the C-shaped portion. The mounting plate may support a rotatable bearing, as shown by FIGS. 2-3 and FIG. 9, with the rotatable bearing configured to provide rotation of a cable guide of the cable swivel assembly. The cable guide may enclose a portion of a cable of the imaging system, and as the C-shaped portion of the C-arm rotates for imaging of a subject, the cable guide may rotate through a range of positions in order to guide the cable away from an imaging area of the C-arm, as shown by FIGS. 4-8. In this way, the cable swivel assembly guides the cable clear of the imaging area, increasing an ease of use of the imaging system and reducing a likelihood of image degradation resulting from cable intrusion into the imaging area.

Turning to FIG. 1, a side view of an imaging system 100 is shown, where the imaging system includes a C-arm 104 with an x-ray source 106 positioned opposite to an x-ray detector 108. The imaging system 100 additionally includes a base unit 102. Base unit supports imaging system 100 at ground surface 190 on which the imaging system 100 sits.

The C-arm 104 includes a C-shaped portion 105 connected to an extended portion 107. The C-shaped portion 105 may be configured to rotate within a range of at least 180 degrees relative to the base unit 102 via a coupling between the C-shaped portion 105 and extended portion 107. For example, the C-arm 104 is rotatable about a rotational axis 164 arranged between the opposing ends of the C-shaped portion 105 (e.g., first end 141 and second end 143) and not intersecting the C-shaped portion 105, and may rotate in a first direction 192 or an opposing, second direction 194. The C-shaped portion 105 may be rotated as described above in order to adjust the x-ray source 106 and detector 108 through a plurality of positions with respect to reference axes 199 (e.g., continuously adjusted throughout a full range of motion of the C-shaped portion 105 around rotational axis 164). x-ray source 106 and detector 108 are positioned on opposite ends of the C-shaped portion of the C-arm 104 along an axis 166, where axis 166 intersects rotational axis 164 and extends radially relative to rotational axis 164. Thus, x-ray source 106 and detector 108 may be rotated about rotational axis 164.

For example, in an initial, first position shown by FIG. 1, the detector 108 is positioned vertically above the x-ray source 106 relative to the ground surface 190 on which the imaging system 100 sits, with axis 166 arranged normal to the ground surface 190 intersecting a midpoint of each of the outlet 111 of x-ray source 106 and detection surface 113 of detector 108. The C-arm 104 may be adjusted from the first position to a different, second position by rotating the C-shaped portion 105 (e.g., via the coupling between extended portion 107 and the C-shaped portion 105). In one example, the second position may be a position in which the x-ray source 106 and detector 108 are rotated 180 degrees together relative to the first position via the rotatable joint, such that the x-ray source 106 is positioned vertically above the detector 108, with axis 166 still intersecting the midpoint of the outlet 111 of the x-ray source 106 and the midpoint of the detection surface 113 of the detector 108. When adjusted to the second position, the x-ray source 106 may be positioned vertically above the rotational axis 164 of the C-shaped portion 105 of the C-arm 104, and the detector 108 may be positioned vertically below the rotational axis 164. As another example, the x-ray source 106 and detector 108 may be rotated together around the rotational axis 164 via the coupling between the extended portion 107 and the C-shaped portion 105 (e.g., as described further below with reference to FIGS. 4-8).

During an imaging operation, a portion of a patient's body placed in a clearance (e.g., gap) formed between the x-ray source 106 and detector 108 may be irradiated with radiation from the x-ray source. For example, x-ray source 106 may comprise an x-ray tube housed within a housing 115, and x-ray radiation generated by the x-ray source 106 may emit from an outlet 111 of the housing 115 and may be intercepted by a detection surface 113 of the detector 108. The radiation may penetrate the portion of the patient's body being irradiated and travel to the detector 108, where the radiation is captured. By penetrating the portion of the patient's body placed between the x-ray source 106 and detector 108, an image of the patient's body is captured and relayed to an electronic controller of the imaging system 100 (e.g., via an electrical connection line) In some examples, imaging system 100 may be used in image-guided surgery, and thus, the patient may be positioned in a sterile field within the gap between the x-ray source 106 and the detector 108. As described further below, a cable swivel assembly 148 may reduce a likelihood of degradation of the sterile field by directing a cable (e.g., cable 140) of the imaging system 100 away from (e.g., outside of) the sterile field. Instructions may entered into the imaging system 100 via one or more input devices for activation of the x-ray source, rotation of the C-arm, etc. The base unit 102 may include the electronic controller (e.g., a control and computing unit) that processes instructions or commands sent from the user input devices during operation of the imaging system 100.

The base unit 102 may also include an internal power source that provides electrical power to operate the imaging system 100. Alternatively, the base unit 102 may be connected to an external electrical power source to power the imaging system 100. A plurality of connection lines (e.g., electrical cables) may be provided to transmit electrical power, instructions, and/or data between the x-ray source 106, detector 108, and the control and computing unit. As shown, imaging system 100 includes cable 140 for transmitting electrical power from the electrical power source (e.g., the internal and/or external source) to the C-arm 104, x-ray source 106, and detector 108. For example, the cable 140 may be a high voltage (HV) cable configured to power the x-ray source 106, detector 108, and/or a motor of the C-arm 104 (e.g., for rotation of the C-shaped portion 105).

In the example shown in FIG. 1, cable 140 extends between the extended portion 107 and the C-shaped portion 105 of the C-arm 104 and is coupled to the C-shaped portion 105 via cable swivel assembly 148. The cable swivel assembly 148 includes a cable guide 142 enclosing a portion of the cable 140 and a mounting base 146 where the cable 140 extends through the cable swivel assembly 148 into an interior of the C-shaped portion 105. As shown, the mounting base 146 may be centrally located on the C-shaped portion 105, at a midpoint between a first end 141 of the C-shaped portion 105 and a second end 143 of the C-shaped portion 105. The cable guide 142 may have an increased rigidity relative to the cable 140 and may enclose a portion of the cable 140 proximate to the mounting base 146. In this configuration, the cable guide 142 provides a rigid inlet for coupling the cable 140 to the mounting base 146 on the C-shaped portion 105. For example, during conditions in which the cable 140 presses against the cable guide 142, the rigidity of the cable guide 142 maintains the shape of the cable guide 142 while the cable 140 may bend relative to the cable guide 142. However, because the cable guide 142 encloses the portion of the cable 140, the portion of the cable 140 housed within the cable guide 142 may not deform (e.g., bend, twist, etc.) during conditions in which other portions of the cable 140 are deformed (e.g., portions of the cable 140 positioned externally relative to an interior of the cable guide 142 that are not enclosed or housed by the cable guide 142). Components that may be included in the cable swivel assembly 148 are described below with respect to FIGS. 2-3.

Although the cable guide 142 is rotatably coupled to the mounting base 146 (e.g., cable guide 142 may rotate relative to the mounting base 146), the mounting base 146 is fixedly coupled to the C-shaped portion 105 of the C-arm 104. In this configuration, the cable guide 142 may rotate (e.g., pivot) relative to the mounting base 146, and because the orientation of the mounting base 146 is fixed relative to the C-shaped portion 105, rotating the cable guide 142 relative to the mounting base 146 also rotates the cable guide 142 relative to the C-shaped portion 105. Because the cable guide 142 encloses the portion of the cable 140 and the cable guide 142 is more rigid than the cable 140, during conditions in which the cable guide 142 rotates, the cable guide 142 acts on the cable 140 to adjust the position of the cable 140 with respect to the C-arm 104 (e.g., rotate the cable 140 relative to the C-shaped portion 105 of the C-arm 104). In this way, the cable guide 142 adjusts (e.g., guides) a position of the cable 140 based on the position of the C-shaped portion 105.

The cable guide 142 may rotate through a plurality of different positions within a rotational plane 182. In order to illustrate an orientation of the rotational plane 182 relative to a rotational plane of the C-shaped portion 105 around rotational axis 164, an inset 180 is provided. The view of the C-arm 104 in FIG. 1 shows the C-shaped portion 105 positioned to rotate around the rotational axis 164 in a rotational plane 188, with the rotational plane 188 being a plane parallel to a plane formed by the z-axis and x-axis of reference axes 199. However, the rotational plane 182 of the cable guide 142 is positioned at an angle 195 relative to the rotational plane 188 of the C-shaped portion 105, where the angle 195 is shown by inset 180. In some examples, the angle 195 may be between 30° to 60°. In other examples, the angle 195 may be between 15° to 75°. As another example, the angle 195 may be 45°. As indicated by reference axes 199, inset 180 shows the rotational plane 188 and rotational plane 182 as viewed from a position vertically above the imaging system 100.

The cable guide 142 may be rotatably coupled to mounting base 146 at an angle relative to inner circumferential surface 178 to which the mounting base 146 mounts (e.g., between 15 degrees and 75 degrees, such as an angle of 45 degrees) and may be rotatable within the rotational plane 182 to a plurality of different positions within a first zone 184. Mounting base 146 may be centered between the opposing ends of the C-shaped portion 105 at the inner circumferential surface 178 (e.g., between first end 141 and second end 143). Further, the cable swivel assembly 148 may include one or more components configured to stop the cable guide 142 from rotating within a second zone 186. In order to further illustrate the rotational plane 182, first zone 184, and second zone 186, an inset 131 shows a flat view of the rotational plane 182 (e.g., from a position normal to the rotational plane 182 along a rotational axis 135). An axis 133 is a vertical axis normal to the ground surface 190 on which the imaging system 100 sits, and rotational axis 135 is an axis around which the cable guide 142 may rotate within the first zone 184. The rotational axis 135 may be arranged at an angle relative to inner circumferential surface 178 of the C-shaped portion 105, where the cable swivel assembly 148 couples to the C-shaped portion 105 at the inner circumferential surface 178. For example, the rotational axis 135 may be arranged non-orthogonal to the inner circumferential surface 178 (e.g., arranged in a non-normal direction not parallel to the inner circumferential surface 178). Rotational axis 135 may additionally be angled relative to the rotational axis 164 and non-orthogonal to the rotational axis 164 (e.g., not parallel or perpendicular to the rotational axis 164 of C-shaped portion 105). In some examples, the angle between the rotational axis 135 and the inner circumferential surface 178 may be between 15 and 75 degrees, and in some examples, the angle may be 45 degrees. In some examples, the angle between the rotational axis 135 and the rotational axis 164 may be between 15 and 75 degrees, and in some examples, the angle may be 45 degrees.

An axis 137 and an axis 139 shown by inset 131 indicate boundaries of the first zone 184, where each of the axis 137 and axis 139 may be angled away from the axis 133 in the rotational plane 182 by an angle 147. The first zone 184 includes a first amount of rotational angle (e.g., a first range of rotation) around the rotational axis 135, and the second zone 186 includes a second amount of rotational angle (e.g., a second range of rotation) around the rotational axis 135, where the first zone 184 and second zone 186 together (e.g., in combination) include 360 degrees of angle (e.g., a full rotational range) around the rotational axis 135. In one example, the first amount of angle around the rotational axis 135 included by the first zone 184 (as indicated by an angle 145 between the axis 137 and the axis 139 at the first zone 184) may be less than 180 degrees (e.g., 160 degrees). In other examples, the angle 145 may be a different amount of degrees (e.g., 170 degrees, 150 degrees, etc.). In this configuration, as the cable guide 142 rotates relative to the C-shaped portion 105 around rotational axis 135, the cable guide 142 may rotate in an arc within the rotational plane 182 (e.g., from the axis 139 to the axis 137, or from a first position between the axis 139 and axis 137 in first zone 184 to a second position between the axis 139 and axis 137 in the first zone, etc.).

Although the cable guide 142 may rotate to any position between the axis 137 and axis 139 within the first zone 184 of the rotational plane 182, the cable guide 142 may be configured to not rotate into any position within the second zone 186. For example, the cable swivel assembly 148 may include one or more components configured to stop a rotation of the cable guide 142 from the first zone 184 to the second zone 186. In some examples, the second zone 186 may extend into an imaging area of the imaging system 100 (e.g., an area between the detector 108 and x-ray source 106 within which a subject to be imaged, such as a patient, may be positioned). As such, rotation of the cable guide 142 into the second zone 186 may be undesirable. By configuring the cable swivel assembly 148 to stop the cable guide 142 from rotating into the second zone 186, a likelihood of intrusion of the cable guide 142 into the imaging area may be reduced, which may increase patient comfort and/or reduce a likelihood of degradation of the imaging system 100 (e.g., reduce a likelihood of de-sterilization of components within the imaging area). For example, the cable guide 142 of the cable swivel assembly 148 may prevent the cable 140 from entering into an interior region 198 (e.g., a keep-out region) defined within the C-arm 104 (e.g., defined by the structure of the C-shaped portion 105 of the C-arm 104, with the interior region 198 including a plane intersecting first end 141 and second end 143 of the C-shaped portion 105, the plane parallel to a plane formed by the z-axis and x-axis of reference axes 199). The interior region 198 may be a region configured to be maintained in a sterile condition during operation of the imaging system 100 (e.g., during imaging of a subject).

Because the cable guide 142 may not rotate into the second zone 186 and the position of the cable 140 is adjusted with the rotation of the cable guide 142, the cable guide 142 may additionally reduce a likelihood of intrusion of the cable 140 into the imaging area and interior region 198 (e.g., reduce a likelihood of bending or hanging of the cable 140 into the imaging area and interior region 198). In this way, the cable swivel assembly 148 adjusts the position of the cable 140 as the C-shaped portion 105 of the C-arm 104 rotates to move the cable 140 away from the imaging area and interior region 198 via the cable guide 142.

A length of the cable guide 142, the angle 195 of the rotational plane 182 and mounting base 146 relative to the rotational plane 188 of the C-shaped portion 105, and a length of cable 140 may each be selected in order to maintain a tension in the cable 140 within a pre-determined range (e.g., a range in which the cable 140 is not overly taut or slacked) for various rotational positions of the C-shaped portion 105 and reduce a likelihood of intrusion of the cable 140 into the imaging area and interior region 198. As one example, the length of cable 140 may be selected to enable cable 140 to bend and/or flex as the C-shaped portion 105 rotates around rotational axis 164 while still enabling the position of the cable 140 to be adjusted via the cable guide 142 during the rotation (e.g., to reduce a likelihood of dragging or pinching of the cable 140). An example configuration of a cable guide that may be the same as the cable guide 142 is further described below with respect to FIG. 3.

During conditions in which the C-shaped portion 105 of the C-arm 104 is rotated for imaging of a subject (e.g., a patient), the C-shaped portion 105 may move through a plurality of different rotational positions. For each rotational position of the C-shaped portion 105, an amount of force (e.g., tension, gravity, etc.) applied to the cable 140 may be different. For example, during conditions in which the C-shaped portion 105 is rotated such that the portion of the cable 140 enclosed by the cable guide 142 is at a lower, first vertical position relative to the ground surface 190 on which the imaging system sits, the cable 140 may have a lower, first amount of tension, and during conditions in which the C-shaped portion 105 is rotated such that the portion of the cable 140 enclosed by the cable guide 142 is at a higher, second vertical position relative to the ground surface 190, the cable 140 may have a higher, second amount of tension. The different amounts of tension may result in different amounts and/or directions of rotation of the cable guide 142, where for each rotational position of the C-shaped portion 105, the cable guide 142 directs the cable 140 away from the imaging area and interior region 198 of the imaging system 100. Example rotations of the C-shaped portion 105 and cable guide 142 are described further below with reference to FIGS. 4-8.

Turning now to FIG. 2, an exploded view 200 of a cable swivel assembly 248 that may be coupled to a C-arm is shown. The cable swivel assembly 248 may be the cable swivel assembly 148 of FIG. 1, in some examples. The cable swivel assembly 248 includes several components that may be the same or similar to the components described above with reference to FIG. 1. For example, the cable swivel assembly 248 includes a mounting base 246 and cable guide 242, which may be the same as the mounting base 146 and cable guide 142 shown by FIG. 1 and described above. Reference axes 298 are included by each of FIGS. 2-3 for comparison of the views shown.

The exploded view 200 shows a first section 242a and a second section 242b of the cable guide 242 in an unassembled configuration (with an assembled configuration of the cable guide 242 shown by an inset 299). The first section 242a and second section 242b may couple together around a cable, such as cable 140 described above, in order to enclose a portion of the cable within an interior of the cable guide 242 between first end 320 and second end 321 (shown by inset 299 and described further below with reference to FIG. 3). Each cable guide section 242a and 242b may form one half of the cable guide 242, for example. The first section 242a and second section 242b may each include portions (e.g., walls) having a curvature (e.g., curvature indicated by arrows 290) shaped to enclose the cable. The exploded view 200 also shows a rear coupling 245 comprising a first portion 245a and a second portion 245b, where the first portion 245a and second portion 245b may be positioned within the interior of the cable guide 242 and may couple together around the enclosed portion of the cable. The first end 320 may form a press-fit or frictional fit around the cable via rear coupling 245, for example, to secure the cable guide 242 to the cable (e.g., maintain the cable in the enclosed position within the cable guide 242). Further, although the mounting base 246 is shown as comprising a first base portion 246a and a second base portion 246b, it should be understood that in some examples, the mounting base 246 may be a single, unitary piece. For example, the mounting base 246 may be comprised of a single monolithic component, where the first base portion 246a and second base portion 246b are molded together as a single unit.

The cable swivel assembly 248 further includes a rotatable bearing 244. The bearing 244 may be an annular disc-shaped component having an opening 260 adapted to receive the cable extending through the cable guide 242 (e.g., during conditions in which the cable guide 242 encloses the portion of the cable). The rotatable bearing 244 may include one or more interior components configured to enable a first section 261 of the bearing 244 to rotate relative to a second section 263 of the bearing 244, where the second section 263 is fixedly coupled to a mounting plate 252. In this configuration, the cable guide 242 may be coupled to the first section 261 of the bearing 244 in order to rotate relative to the second section 263 and mounting plate 252, and the cable may extend through the cable guide 242, through the opening 260 of the bearing 244, and through an opening 262 of the mounting plate.

The bearing 244 may include one or more stops or other components configured to enable rotation of the first section 261 within a first range and to disable rotation of the first section 261 within a second range. As one example, when the cable guide 242 is coupled to the bearing 244 (e.g., fixedly coupled to the first section 261), the bearing 244 may enable the cable guide 242 to rotate within a first zone (e.g., the first zone 184 shown by FIG. 1 and described above) and prevent the cable guide 242 from rotating within a second zone (e.g., the second zone 186 shown by FIG. 1 and described above). In this way, the bearing 244 may limit the rotation of the cable guide 242 (e.g., limit a rotation angle of the cable guide 242).

The cable swivel assembly 248 includes a plurality of mounting brackets configured to secure the cable swivel assembly 248 to a C-arm of an imaging system (e.g., C-arm 104 of imaging system 100 described above). Mounting plate 252 may be supported by a mounting bracket 253 and a mounting bracket 254 in order to mount to the C-arm at an angle relative to a rotational plane of a C-shaped portion of the C-arm (e.g., angle 195 shown by FIG. 1 and described above). The mounting plate 252 may support the cable guide 242 via the bearing 244, with the bearing 244 forming an interface between the mounting plate 252 and cable guide 242. The mounting plate 252, bearing 244, mounting bracket 253, and mounting bracket 254 may be at least partially housed within the mounting base 246. The mounting bracket 253 and mounting bracket 254 may couple directly to the C-shaped portion of the C-arm and may further couple to the mounting base 246 in order to maintain the mounting base 246 in position relative to the C-arm. In one example, the mounting bracket 253 and mounting bracket 254 may be coupled to the C-shaped portion of the C-arm via fasteners (e.g., bolts, screws, etc.) inserted through openings of the mounting brackets aligned with corresponding openings of the C-shaped portion of the C-arm. The mounting plate 252 may be coupled to the mounting bracket 253 and mounting bracket 254 via fasteners (e.g., bolts, screws, etc.) inserted through openings of the mounting plate 252 aligned with corresponding openings of the mounting bracket 253 and mounting bracket 254.

Each mounting bracket includes a mounting surface (e.g., mounting surface 275) configured to be coupled in face-sharing contact with an inner circumferential surface of the C-shaped portion of the C-arm (e.g., inner circumferential surface 178 shown by FIG. 1). In this configuration, the mounting base 246 is coupled to the inner circumferential surface by the mounting brackets (e.g., mounting bracket 253 and mounting bracket 254). Each mounting bracket further includes an angled surface, such as angled surface 279, positioned at an angle 273 relative to the mounting surface (e.g., mounting surface 275). The angled surface is configured to couple in face-sharing contact with the mounting plate 252 in order to maintain the mounting plate 252 at angle 273 relative to the inner circumferential surface of the C-shaped portion of the C-arm. In some examples, the angle 273 may be between 30 degrees and 60 degrees. In one example, the angle 273 is 45 degrees.

Referring to FIG. 3, a cross-sectional view of the cable swivel assembly 248 described above with reference to FIG. 2 is shown. FIG. 3 shows cable swivel assembly 248 in an assembled configuration. The rear coupling 245 is shown coupled at first end 320 of the cable guide 242, where the rear coupling 245 includes an opening 322 adapted to receive the cable enclosed by the cable guide (e.g., cable 140 described above). In the view shown by FIG. 3, a position of the cable within a cable passage 355 of the cable guide 242 is indicated by dashed lines 340, where the cable has a diameter 341 (e.g., as indicated by the length between the dashed lines 340). Cable passage 355 extends through first end 320 of the cable guide 242 to second end 321 of the cable guide 242 and is configured to enclose the portion of the cable. The opening 322 at the rear coupling 245 may have approximately a same diameter 323 as the cable (e.g., substantially diameter 341) such that when the cable guide 242 is coupled around the cable (e.g., to enclose the portion of the cable), the rear coupling 245 may be in face-sharing contact with outer surfaces of the cable to maintain the position of the portion of the cable at the opening 322.

Second end 321 of the cable guide 242 includes an opening formed between end surfaces 360 and having a second diameter 325 (also shown by FIG. 2), where the second diameter 325 may be larger than the diameter 323. The second diameter 325 may be approximately the same as (e.g., a same amount of length) or larger than a diameter 270 of the bearing 244 (shown by FIG. 2). In this configuration, the bearing 244 may seat within the opening at the second end 321. The opening 260 may have a diameter 331 larger than the diameter 341 of the cable, such that a small clearance may be formed between the cable and the surfaces of the bearing 244 forming the opening 260 during conditions in which the cable extends through the opening 260. The clearance between the surfaces forming the opening 260 and the cable may reduce a likelihood of binding of the cable within the cable guide 242 and/or bearing 244. The opening 260 of the bearing 244 may be positioned at the opening of the cable guide 242 at the second end 321 and arranged concentrically relative to the opening of the cable guide 242 at the second end 321 (e.g., centered relative to the opening of the cable guide 242 at the second end 321), with the opening 260 of the bearing 244 adapted to guide the cable from an interior 350 of the cable guide 242 to an interior 352 of the mounting base 246.

The rear coupling 245 is partially enclosed by the cable guide 242 at the first end 320, with a lip portion 354 of the rear coupling 245 maintaining a position of the rear coupling 245 relative to the cable guide 242. A diameter of the lip portion 354 may be larger than diameter 323 of the opening 322 of the rear coupling 245, with the lip portion 354 configured to seat against an end surface 356 of the cable guide 242 at first end 320. The cable guide 242 is open at the first end 320, with the end surface 356 forming a circumference of the opening of the cable guide 242 at the first end 320. The end surface 356 is a circumferential surface formed around a clearance 358 between first side 380 and second side 382 of the cable guide 242, with rear coupling 245 shaped to seat within the clearance 358 to couple to the cable guide 242 (e.g., with the lip portion 354 of the rear coupling 245 abutting the end surface 356). In some examples, the rear coupling 245 may be friction-fit within the first end 320 of the cable guide 242 and arranged in face-sharing contact with inner surfaces of the cable guide 242.

The cable guide 242 is coupled to the bearing 244, with the bearing 244 forming an interface between the cable guide 242 and the mounting base 246 such that the cable guide 242 may rotate relative to the mounting base 246 (e.g., via rotation of the first section 261 of the bearing 244 relative to the second section 263 of the bearing 244, as described above). In some examples, the cable guide 242 is coupled to the first section 261 of the bearing 244 via fasteners 372 (e.g., bolts, screws, etc.).

The cable guide 242 is shaped such that the interior 350 of the cable guide 242 comprises a plurality of curved walls, such as a wall 377 of first section 242a coupled to a corresponding curved wall of the second section 242b (e.g., as indicated in FIG. 2, with arrows 290 illustrating a curvature of the wall 377 at first end 320). The walls may curve from the first end 320 to the second end 321 in order to guide the cable through the cable guide 242 from the first end 320 to the second end 321. During conditions in which the portion of the cable is enclosed by the cable guide 242, the cable may curve within the cable guide 242 with a curvature 375. First side 380 of the cable guide 242 may be positioned further than opposing, second side 382 of the cable guide 242 in a direction of a rotational axis 370 of the cable guide 242 (e.g., similar to the rotational axis 135 described above with reference to FIG. 1).

The walls forming the interior 350 of the cable guide 242 may curve with different curvature at each of the first side 380 and second side 382. For example, wall 377 includes a portion arranged at the first side 380 and a portion arranged at the second side 382 (e.g., due to the circumferential curvature of the wall 377, as indicated by arrows 290 in FIG. 2, around an axis 371 arranged radially relative to the rotational axis 370, as shown by FIG. 3). The portion of the wall 377 arranged at the first side 380 curves toward the second end 321 with a first curvature 374 (e.g., first radius of curvature) and the portion of the wall 377 arranged at the second side 382 curves toward the second end 321 with a different, second curvature 376 (e.g., second radius of curvature). By curving with the different curvatures at the first side 380 and second side 382, wall 377 forms a rigid, elongate portion 379 of the cable guide 242 configured to engage the cable and within which the cable may be maintained in an approximately straight configuration (e.g., a straightened configuration in which the cable extends straight through the interior 350 of the cable guide 242 without bending or twisting).

The wall 377 may include a first straight portion 385 arranged at the first side 380 and a second straight portion 386 arranged at the second side 382, where the first straight portion 385 and second straight portion 386 are positioned approximately parallel with each other and parallel to axis 371 extending radially relative to rotational axis 370. The first straight portion 385 and second straight portion 386 each terminate at the first end 320 and form end surface 356. An amount of the curvature 374 and curvature 376, as well as a length of the first straight portion 385 and a length of the second straight portion 386, may be selected in order to control a size (e.g., length) of the elongate portion 379. In some examples, the size of the elongate portion 379 may be selected in order to reduce a likelihood of intrusion of the cable guide 242 and the cable partially enclosed by the cable guide 242 into an imaging area and interior region (e.g., interior region 198 described above) of an imaging system including the cable guide (e.g., imaging system 100 shown by FIG. 1 and described above) when the cable guide 242 is rotated relative to the C-shaped portion of the C-arm of the imaging system.

In some examples, the cable guide 242 may include an inner surface protrusion 347 configured to guide an internal position of the cable within the cable guide 242 (e.g., between the opposing sides of the wall 377, with the portion of the wall 377 at the first side 380 having the curvature 374, and with the portion of the wall 377 at the second side 382 having the curvature 376). For example, because the diameter 325 of cable guide 242 at the second end 321 is sized to accommodate the bearing 244, the inner surface protrusion 347 may provide a smaller inner diameter for creating a desired curvature of the cable from the elongate portion 379 to the second end 321. The desired curvature may reduce a likelihood of pinching of the cable within the cable guide 242 as the cable is guided by the cable guide between the first end 320 and second end 321 (e.g., through elongate portion 379 and curving toward second end 321). For example, the opening at the second end 321 of the cable guide 242 may be arranged perpendicular to the opening of the cable guide 242 at the first end 320, and the protrusion 347 may gradually guide the cable from the first end 320 to the second end 321 with curvature 375.

As described above, the second end 321 of the cable guide 242 is coupled to the first section 261 of the bearing 244. The opening 260 of the bearing 244 is a passage formed by the first section 261 and extending through the second section 263 of the bearing 244. When the first section 261 rotates relative to the second section 263 around rotational axis 370, the cable guide 242 similarly rotates along with the first section 261 around rotational axis 370. Because the opening 260 of the first section 261 extends through the second section 263, the cable may extend through each of the first section 261 and second section 263 by extending through the opening 260. The portion of the cable disposed within the opening 260 may thus similarly rotate with the first section 261 and cable guide 242 when the first section 261 and cable guide 242 are rotated around rotational axis 370.

As mentioned above, the bearing 244 may not have a full 360 degree rotation about the rotational axis 370, but may rotate within a pre-determined zone (e.g., first zone 184 described above with reference to FIG. 1) based on a position of a stop within the bearing 244. The stop may comprise a component of the first section 261 configured to interfere with a component of the second section 263 when rotation of the cable guide 242 outside of the pre-determined zone is attempted, as described further below with reference to FIG. 9. For example, the stop may prevent the first section 261 from further rotating with respect to the second section 263 around the rotational axis 370 when a boundary of the pre-determined zone is reached. Similar to the examples discussed below with reference to FIGS. 4-8, the stop may maintain a position of the cable guide 242 for some rotational positions of the C-shaped portion of the C-arm. For example, during conditions in which the C-shaped portion is rotated such that the cable guide 242 is positioned vertically above a rotational axis of the C-shaped portion (e.g., at a vertically higher position than the rotational axis, relative to a ground surface on which the imaging system sits), the stop may maintain the rotational position of the cable guide 242 relative to the C-shaped portion in order to position the cable guide, and the cable partially enclosed by the cable guide, outside of the imaging area and interior region of the imaging system.

Referring to FIGS. 4-8, the imaging system 100 described above with reference to FIG. 1 is shown with the C-shaped portion 105 of C-arm 104 rotated to various positions about the rotational axis 164. Some components introduced in FIG. 1 are not numbered in FIGS. 4-8 for illustrative clarity, although it should be understood that such components may be present.

As described above, the cable guide 142 of the imaging system 100 may rotate based on the rotational position of the C-shaped portion 105 of the C-arm 104 in order to position the cable 140 of the imaging system 100 outside of the imaging area and interior region of the C-arm 104. FIGS. 4-8 illustrate a position of the cable guide 142 for various rotational positions of the C-shaped portion 105. In the examples described herein, the position of the cable guide 142 may be adjusted via force applied to the cable guide 142 by the cable 140 (e.g., a tension and/or weight of the cable 140) along with force applied to the cable guide 142 by gravity. For example, the cable guide 142 includes an elongate portion 402 similar to the elongate portion 379 of the cable guide 242 described above with reference to FIGS. 2-3. The elongate portion 402 extends away from the rotational axis 135 of the cable guide 142, and as a result, torque may be applied to the elongate portion 402 by gravity. The force (e.g., torque) applied to the cable guide 142 by gravity, along with the force applied to the cable guide 142 by the cable 140, may together automatically (e.g., via gravity and force applied by the cable 140, without driving the cable guide 142 by motor) rotate the cable guide 142 relative to the C-arm 104 based on the rotational position of the C-shaped portion 105 of the C-arm 104. For example, the cable guide 142 may be rotated without actuating a motor to drive the rotation of the cable guide 142 and without force applied to the cable guide 142 by a user of the imaging system 100, such as a clinician.

Turning first to FIG. 4, a first position 400 of C-arm 104 is shown (e.g., a first rotational position of the C-shaped portion 105). In the first position 400, the mounting base 146 is positioned proximate to the ground surface 190 and a length (e.g., distance) between the detector 108 and extended portion 107 is less than a length between the x-ray source 106 and extended portion. In the first position 400, the axis 166 between the x-ray source 106 and the detector 108 is arranged parallel to the ground surface 190. In this configuration, the cable guide 142 adjusts the position of the cable 140 such that the cable 140 extends toward the base unit 102 and away from the imaging area and interior region of the imaging system 100 (e.g., the open area disposed between the detector 108 and the x-ray source 106 and between the opposing ends (first end 141 and second end 143) of the C-shaped portion 105). In one example, the position of the cable guide 142 in FIG. 4 may be a position in which the elongate portion 402 of the cable guide 142 extends along axis 137 (e.g., parallel to axis 137) in the first zone 184, with the axis 137 and first zone 184 shown by FIG. 1 and described above.

FIG. 5 shows C-arm 104 in a second position 500 (e.g., a second rotational position of the C-shaped portion 105). The second position 500 may correspond to a position of the C-shaped portion 105 in which the C-shaped portion 105 is rotated by 45 degrees around the rotational axis 164 from the first position 400 shown in FIG. 4 (e.g., rotated clockwise relative to the view shown by FIG. 4). In the second position 500, the detector 108 is positioned more proximate to the extended portion 107 than the x-ray source 106, but is less proximate to the extended portion 107 relative to the first position 400. Further, the x-ray source 106 is positioned more proximate to the ground surface 190 in the second position 500 relative to the first position 400. The position of the cable guide 142 in FIG. 5 may be a position in which the elongate portion 402 of the cable guide 142 extends in a direction between the axis 137 and the axis 139 in the first zone 184, with the axis 137, axis 139, and first zone 184 shown by FIG. 1 and described above. For example, as described above, the angle 145 between the axis 137 and the axis 139 may be 160 degrees (e.g., with 0 degrees corresponding to a location along the axis 137 and with 160 degrees corresponding to a location along the axis 139), and in the second position 500 shown by FIG. 5, the elongate portion 402 of the cable guide 142 may extend at 80 degrees within the first zone 184 (e.g., along midway axis 167 between axis 137 and axis 139).

FIG. 6 shows C-arm 104 in a third position 600 (e.g., a third rotational position of the C-shaped portion 105), which may be a position corresponding to 45 degrees of rotation of the C-shaped portion 105 in the clockwise direction relative to the second position 500 shown by FIG. 5. In the third position 600, the mounting base 146 is positioned proximate to the extended portion 107, and the x-ray source 106 is positioned proximate to the ground surface 190, with the axis 166 between the x-ray source 106 and the detector 108 arranged perpendicular (e.g., normal) to the ground surface 190. The position of the cable guide 142 in FIG. 6 may be a position in which the elongate portion 402 of the cable guide 142 extends in along the axis 139 in the first zone 184, with the axis 139 and first zone 184 shown by FIG. 1 and described above.

FIG. 7 shows C-arm 104 in a fourth position 700 (e.g., a fourth rotational position of the C-shaped portion 105), which may be a position corresponding to 45 degrees of rotation of the C-shaped portion 105 in the clockwise direction relative to the third position 600 shown by FIG. 6. In the fourth position 700, the x-ray source is positioned more proximate to the extended portion 107 than the detector 108. Further, the detector 108 is positioned farther from the extended portion 107 relative to the third position 600 shown by FIG. 6. The position of the cable guide 142 in FIG. 7 may be a position in which the elongate portion 402 of the cable guide 142 extends in along the axis 139 in the first zone 184, with the axis 139 and first zone 184 shown by FIG. 1 and described above. As the C-arm 104 transitions from the third position 600 shown by FIG. 6 to the fourth position 700 shown by FIG. 7, the cable guide 142 may be maintained in the same rotational position due to engagement of one or more stops of a bearing of the cable swivel assembly 148 (e.g., bearing 244 described above). For example, as described above with reference to FIG. 1, the cable guide 242 may rotate within the first zone 184 but may not rotate within the second zone 186. Although forces (e.g., gravity, cable tension, etc.) may act on the cable guide 142 as the C-arm 104 transitions from the third position 600 to the fourth position 700, the cable guide 142 does not rotate during the transition due to the engagement of the one or more stops. Specifically, the position of the elongate portion 402 along axis 139 may be maintained as the C-arm 104 transitions from the third position 600 to the fourth position 700, and even though forces acting on the cable guide 142 (e.g., gravity, cable tension, etc.) may urge the cable guide 142 to rotate toward the second zone 186, the cable guide 142 does not rotate into the second zone 186 and remains in the first zone 184 due to the engagement of the one or more stops of the bearing of the cable swivel assembly 148.

FIG. 8 shows C-arm 104 in a fifth position 800 (e.g., a fifth rotational position of the C-shaped portion 105), which may be a position corresponding to 45 degrees of rotation of the C-shaped portion 105 in the clockwise direction relative to the fourth position 700 shown by FIG. 7. In the fifth position 800, the mounting base 146 is positioned farther from the ground surface 190 than each of the x-ray source 106 and detector 108. Further, the x-ray source 106 is positioned more proximate to the extended portion 107 than the detector 108. Axis 166 between the x-ray source 106 and the detector 108 is arranged parallel to the ground surface 190 in the fifth position 800, similar to the first position 400. However, in the fifth position 800, the C-shaped portion 105 is rotated 180 degrees relative to the first position 400. The position of the cable guide 142 in FIG. 8 may be a position in which the elongate portion 402 of the cable guide 142 extends along the axis 139 in the first zone 184, with the axis 139 and first zone 184 shown by FIG. 1 and described above. As the C-arm 104 transitions from the fourth position 700 shown by FIG. 7 to the fifth position 800 shown by FIG. 8, the cable guide 142 may be maintained in the same rotational position due to engagement of the one or more stops of the bearing of the cable swivel assembly 148 (e.g., bearing 244 described above), similar to the example described above with reference to the transition from the third position 600 to the fourth position 700.

By configuring the cable guide 142 to rotate as described above based on the rotational position of the C-shaped portion 105 of the C-arm 104, the cable guide 142 maintains the cable 140 in a position outside of the imaging area and interior region of the imaging system 100 and away from the space between the opposing ends of the C-shaped portion 105. For example, the cable guide 142 may maintain the cable 140 away from the axis 166 between the detector 108 and the x-ray source 106 for each rotational position of the C-arm 104. In this way, a likelihood of intrusion of the cable 140 into the interior region (and imaging area) may be reduced, which may increase patient comfort and/or reduce a likelihood of degradation of the imaging system 100 (e.g., reduce a likelihood of de-sterilization of components within the interior region and imaging area).

Referring now to FIG. 9, a perspective view of bearing 244 and mounting plate 252 introduced in FIG. 2 is shown. As such, components of FIG. 9 previously introduced in FIG. 2 are numbered the same and will not be reintroduced. As described above, bearing 244 includes first section 261 and second section 263, with second section 263 fixedly coupled (e.g., non-rotationally coupled) to the mounting plate 252, and with first section 261 rotationally coupled to the second section 263. Bearing 244 is illustrated without a cover plate portion in FIG. 9, although in some examples the bearing 244 may include the cover plate portion (e.g., similar to the view shown by FIG. 2).

The first section 261 includes a protrusion 900. When the first section 261 is rotated relative to the second section 263, the protrusion 900 may engage with one or more stops of the second section 263 in order to prevent a rotation of the first section 261 through a pre-determined zone (e.g., second zone 186 shown by FIG. 1 and described above). In the example shown by FIG. 9, the second section 263 includes a first stop 902 and a second stop 904, with axis 910 extending radially relative to rotational axis 370 through the first stop 902, and with axis 912 extending radially relative to rotational axis 370 through the second stop 904.

The first section 261 may rotate to any of a continuous plurality of different positions between the first stop 902 and second stop 904 within a first zone of the bearing 244, with the first zone indicated by arrows 920 extending at a first side 930 of the bearing around rotational axis 370 and between the axis 910 and axis 912. However, the first section 261 may not rotate to any position within a second zone of the bearing 244, with the second zone indicated by arrows 922 extending at an opposing, second side 932 of the bearing around rotational axis 370 and between the axis 910 and axis 912. In some examples, the axis 910 may be the same as the axis 137 described above with reference to FIG. 1 and FIGS. 4-8, and the axis 912 may be the same as the axis 139 described above with reference to FIG. 1 and FIGS. 4-8. In one example, the first section 261 may rotate relative to the second section 263 by 160 degrees within the first zone. For example, the first section 261 may be rotatable relative to the second section 263 to a first position with the protrusion 900 engaged with the first stop 902 at the first side 930, a second position with the protrusion 900 engaged with the second stop 904 at the first side 930, and a continuous plurality of intermediate positions between the first position and second position at the first side 930. In some examples, the first position and second position may be separated by 180 degrees of rotation or less (e.g., 160 degrees of rotation, as described above).

By configuring the first section 261 to rotate only within the first zone and not within the second zone, the bearing 244 enables the cable guide 242 (shown by FIGS. 2-3) to rotate the cable of the imaging system outside of the imaging area and interior region of the imaging system as the C-shaped portion of the C-arm of the imaging system is rotated (e.g., similar to the examples described above with reference to FIGS. 4-8). Additionally, when the C-shaped portion is rotated and the cable guide does not rotate (e.g., due to engagement of the protrusion 900 with the first stop 902 or second stop 904), the bearing 244 maintains the position of the cable guide 242 to guide the cable away from the imaging area and interior region.

The technical effect of coupling the cable guide to the mounting base of the cable swivel assembly at an angle relative to the rotational plane of the C-shaped portion of the C-arm, and configuring the cable guide to rotate within the first zone and not the second zone, is to move the cable and cable guide away from the imaging area and interior region of the imaging system during conditions in which the C-shaped portion is rotated to image a subject. In this way, the cable swivel assembly guides the cable and cable guide clear of the imaging area and interior region, increasing an ease of use of the imaging system and reducing a likelihood of image degradation resulting from cable intrusion into the imaging area and interior region.

In one embodiment, an assembly for a C-arm imaging system comprises: a cable guide configured to rotate around a rotational axis arranged at an angle to a surface of a C-shaped portion of the C-arm imaging system to which the assembly mounts, the cable guide including a rigid elongate portion extending outward from the rotational axis and configured to enclose a portion of a cable of the C-arm imaging system. In a first example of the assembly, the assembly further comprises a cable passage extending through a first end of the cable guide to a second end of the cable guide, the cable passage enclosing the portion of the cable, with the cable guide configured to engage the cable at the first end via the rigid elongate portion and to rotate around the rotational axis at the second end. A second example of the assembly optionally includes the first example, and further includes wherein the first end press-fits to the cable with a smaller, first diameter, and the second end spaces apart from the cable with a larger, second diameter. A third example of the assembly optionally includes one or both of the first and second examples, and further includes wherein the rotational axis of the cable guide is non-orthogonal to the surface of the C-shaped portion. A fourth example of the assembly optionally includes one or more or each of the first through third examples, and further includes wherein the angle of the rotational axis to the surface of the C-shaped portion is between 30 degrees and 60 degrees. A fifth example of the assembly optionally includes one or more or each of the first through fourth examples, and further includes wherein the cable guide is rotatable around the rotational axis only by 180 degrees or less.

In one embodiment, a system comprises: a C-arm; a cable coupled to an electronic controller of the C-arm; and a cable swivel assembly configured to adjust a position of the cable relative to the C-arm, including: a base including a mounting surface fixedly coupled to the C-arm; a cable guide enclosing a portion of the cable and rotatably coupled to the base at an angle relative to the mounting surface; and an interface between the cable guide and the base including a pair of stops configured to limit a rotation of the cable guide. In a first example of the system, the cable guide includes a rigid elongate portion formed at a first end of the cable guide, with the portion of the cable enclosed by the cable guide seated within the rigid elongate portion in a straightened configuration. A second example of the system optionally includes the first example, and further includes wherein the first end is press-fit to the cable and the cable guide includes a second end rotatably coupled to the base via the bearing, with the cable curving through the cable guide from the rigid elongate portion to the second end. A third example of the system optionally includes one or both of the first and second examples, and further includes wherein the C-arm includes a C-shaped portion having an x-ray source and an x-ray detector coupled at opposing ends of the C-shaped portion, with the cable swivel assembly coupled to the C-arm at the C-shaped portion. A fourth example of the system optionally includes one or more or each of the first through third examples, and further includes wherein the mounting surface is coupled to an inner circumferential surface of the C-shaped portion and the base is centered between the opposing ends, and a rotational axis of the cable guide is not normal or parallel to the inner circumferential surface. A fifth example of the system optionally includes one or more or each of the first through fourth examples, and further includes wherein the C-shaped portion is rotatable around a first rotational axis arranged between the opposing ends of the C-shaped portion and not intersecting the C-shaped portion, and the cable guide is rotatable around a second rotational axis angled relative to the first rotational axis and non-orthogonal to the first rotational axis. A sixth example of the system optionally includes one or more or each of the first through fifth examples, and further includes wherein the second rotational axis is angled 45 degrees relative to the first rotational axis. A seventh example of the system optionally includes one or more or each of the first through sixth examples, and further includes where the interface is a bearing including a first section fixedly coupled to the cable guide and a second section fixedly coupled to the base, the first section rotatable relative to the second section and the second section including the pair of stops, where the first section includes a protrusion disposed between the pair of stops at a first side of the bearing. A seventh example of the system optionally includes one or more or each of the first through sixth examples, and further includes wherein the first section is rotatable relative to the second section only to a first position with the protrusion engaged with the first stop at the first side, a second position with the protrusion engaged with the second stop at the first side, and a continuous plurality of intermediate positions between the first position and second position at the first side.

In one embodiment, a method comprises: coupling a cable guide around a cable of a C-arm of an imaging system; and limiting a rotation angle of the cable guide while rotating the cable guide relative to the C-arm. In a first example of the method, rotating the cable guide relative to the C-arm includes rotating the cable guide around a rotational axis arranged non-orthogonal to a mounting surface of the C-arm, the cable guide rotatably coupled to the C-arm at the mounting surface. A second example of the method optionally includes the first example, and further includes wherein coupling the cable guide around the cable includes enclosing a portion of the cable between a first section and a second section of a rigid elongate portion of the cable guide. A third example of the method optionally includes one or both of the first and second examples, and further includes wherein rotating the cable guide relative to the C-arm includes rotating the cable guide via gravity and without driving the cable guide by motor. A fourth example of the method optionally includes one or more or each of the first through third examples, and further includes wherein limiting the rotation angle of the cable guide while rotating the cable guide relative to the C-arm includes: allowing rotation of the cable guide to a first fully rotated position, a second fully rotated position, and a continuous plurality of intermediate rotated positions between the first fully rotated position and second fully rotated position, with the first fully rotated position and second fully rotated position separated by 180 degrees of rotation or less; and stopping the cable guide from rotating beyond the first fully rotated position or second fully rotated position.

In another representation, a cable swivel assembly comprises: a base including a mounting surface and an angled surface; and a cable guide including a first end forming a cable passage and a second end rotatably coupled to the base at the angled surface.

In another representation, a method comprises: rotating a C-shaped portion of a C-arm around a first rotational axis; and controlling a position of a cable coupled to the C-arm via a cable swivel assembly based on the rotation of the C-shaped portion. In a first example of the method, controlling the position of the cable coupled to the C-arm via the cable swivel assembly based on the rotation of the C-shaped portion includes controlling a rotational position of a cable guide of the cable swivel assembly coupled to the cable based on a rotational range of the cable guide. A second example of the method optionally includes the first example, and further includes wherein controlling the rotational position of the cable guide of the cable swivel assembly based on the rotational range of the cable guide includes: while rotating the C-shaped portion to any of a first plurality of rotated positions, adjusting the rotational position of the cable guide; and while rotating the C-shaped portion to any of a second plurality of rotated positions, maintaining the rotational position of the cable guide. A third example of the method optionally includes one or both of the first and second examples, and further includes wherein the first plurality of rotated positions of the C-shaped portion includes a first fully rotated position, and the second plurality of rotated positions of the C-shaped portion includes a second fully rotated position. A fourth example of the method optionally includes one or more or each of the first through third examples, and further includes wherein the first plurality of rotated positions includes a first intermediate position between the first fully rotated position and second fully rotated position, and the second plurality of rotated positions includes a second intermediate position between the first intermediate position and second fully rotated position. A fifth example of the method optionally includes one or more or each of the first through fourth examples, and further includes wherein adjusting the rotational position of the cable guide includes rotating the cable guide relative to the C-shaped portion around a second rotational axis arranged non-orthogonal and non-parallel to the first rotational axis. A sixth example of the method optionally includes one or more or each of the first through fifth examples, and further includes wherein rotating the cable guide relative to the C-shaped portion includes rotating a first section of a bearing of the cable swivel assembly around the second rotational axis relative to a second section of the bearing, the first section rotationally fixed to the cable guide and the second section rotationally fixed to the C-shaped portion. A seventh example of the method optionally includes one or more or each of the first through sixth examples, and further includes wherein rotating the cable guide relative to the C-shaped portion includes rotating the cable guide via gravity and without driving the cable guide by motor. An eighth example of the method optionally includes one or more or each of the first through seventh examples, and further includes wherein controlling the rotational position of the cable guide of the cable swivel assembly based on the rotational range of the cable guide includes adjusting the rotational position of the cable guide to a first rotational end position relative to the C-shaped portion while the C-shaped portion is in a first fully rotated position. A ninth example of the method optionally includes one or more or each of the first through eighth examples, and further includes wherein controlling the rotational position of the cable guide of the cable swivel assembly based on the rotational range of the cable guide includes adjusting the rotational position of the cable guide to a transitional position relative to the C-shaped portion while the C-shaped portion is between the first fully rotated position and first intermediate position. A tenth example of the method optionally includes one or more or each of the first through ninth examples, and further includes wherein controlling the rotational position of the cable guide of the cable swivel assembly based on the rotational range of the cable guide includes adjusting the rotational position of the cable guide to a second rotational end position relative to the C-shaped portion while the C-shaped portion is at the first intermediate position. An eleventh example of the method optionally includes one or more or each of the first through tenth examples, and further includes wherein controlling the rotational position of the cable guide of the cable swivel assembly based on the rotational range of the cable guide includes maintaining the rotational position of the cable guide at the second rotational end position relative to the C-shaped portion while the C-shaped portion is between the first intermediate position and the second fully rotated position. A twelfth example of the method optionally includes one or more or each of the first through eleventh examples, and further includes wherein controlling the rotational position of the cable guide of the cable swivel assembly based on the rotational range of the cable guide includes maintaining the rotational position of the cable guide at the second rotational end position relative to the C-shaped portion while the C-shaped portion is at the second fully rotated position. A thirteenth example of the method optionally includes one or more or each of the first through twelfth examples, and further includes wherein the first fully rotated position corresponds to 0 degrees of rotation, the first intermediate position corresponds to 90 degrees of rotation, and the second fully rotated position corresponds to 180 degrees of rotation around the first rotational axis.

FIGS. 1-9 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An assembly for a C-arm imaging system, comprising:
a C-arm;
a mounting base;
a cable guide that operates to prevent a cable of the C-arm imaging system from entering an interior region defined within the C-arm on the C-arm imaging system, wherein the cable is positioned within the cable guide, and wherein the cable guide is coupled to the C-arm via the mounting base and configured to rotate relative to the C-arm;
wherein the cable guide is configured to rotate around a rotational axis arranged at an angle to a surface of a C-shaped portion of the C-arm of the C-arm imaging system to which the assembly mounts, the cable guide including a rigid elongate portion extending outward from the rotational axis and configured to enclose a portion of the cable of the C-arm imaging system; and
wherein the angle of the rotational axis to the surface of the C-shaped portion is between 15 degrees and 75 degrees.

2. The assembly of claim 1, further comprising a cable passage extending through a first end of the cable guide to a second end of the cable guide, the cable passage enclosing the portion of the cable, with the cable guide configured to engage the cable at the first end via the rigid elongate portion and to rotate around the rotational axis at the second end.

3. The assembly of claim 1, wherein the mounting base is fixedly coupled to the C-shaped portion of the C-arm, wherein the mounting base is rotatably coupled to the cable guide, and wherein the C-shaped portion of the C-arm and the cable guide are coupled together via the mounting base.

4. The assembly of claim 2, wherein the first end press-fits to the cable with a smaller, first diameter, and the second end spaces apart from the cable with a larger, second diameter.

5. A system, comprising:
a C-arm;
a cable coupled to a power source of the C-arm; and
a cable swivel assembly configured to adjust a position of the cable relative to the C-arm, including:
a base including a mounting surface fixedly coupled to the C-arm;
a cable guide enclosing a portion of the cable and rotatably coupled to the base at an angle relative to the mounting surface, wherein the cable guide is configured to rotate relative to the C-arm, and wherein the cable guide is coupled to the C-arm via the base; and
an interface between the cable guide and the base including a pair of stops configured to limit a rotation of the cable guide, wherein the interface is a bearing and wherein the pair of stops extend from the bearing.

6. The system of claim 5, wherein the cable guide includes a rigid elongate portion formed at a first end of the cable guide, with the portion of the cable enclosed by the cable guide seated within the rigid elongate portion in a straightened configuration.

7. The system of claim 5, wherein the base is coupled to a C-shaped portion of the C-arm.

8. The system of claim 5, wherein the interface is a bearing including a first section fixedly coupled to the cable guide and a second section fixedly coupled to the base, the first section rotatable relative to the second section and the second section including the pair of stops, where the first section includes a protrusion disposed between the pair of stops at a first side of the bearing.

9. The system of claim 6, wherein the first end is press-fit to the cable and the cable guide includes a second end rotatably coupled to the base via the bearing, with the cable curving through the cable guide from the rigid elongate portion to the second end.

10. The system of claim 7, wherein the mounting surface is coupled to an inner circumferential surface of the C-shaped portion and the base is centered between opposing ends of the C-shaped portion, and a rotational axis of the cable guide is not normal or parallel to the inner circumferential surface.

11. The system of claim 7, wherein the C-shaped portion is rotatable around a first rotational axis arranged between opposing ends of the C-shaped portion and not intersecting the C-shaped portion, and the cable guide is rotatable around a second rotational axis angled relative to the first rotational axis and non-orthogonal to the first rotational axis.

12. The system of claim 11, wherein the second rotational axis is angled between 15 degrees and 75 degrees relative to the first rotational axis.

13. The system of claim 8, wherein the first section is rotatable relative to the second section only to a first position with the protrusion engaged with a first stop of the pair of stops at the first side, a second position with the protrusion engaged with a second stop of the pair of stops at the first side, and a continuous plurality of intermediate positions between the first position and second position at the first side.

14. A method, comprising:
providing a C-arm for an imaging system and a cable supplying power to the C-arm;
coupling a cable guide around the cable of the C-arm, wherein the cable guide is coupled to the C-arm and configured to rotate relative to the C-arm;
rotating the cable guide relative to the C-arm; and
limiting a rotation angle of the cable guide while rotating the cable guide relative to the C-arm, wherein limiting the rotation angle of the cable guide while rotating the cable guide relative to the C-arm includes:
allowing rotation of the cable guide to a first fully rotated position, a second fully rotated position, and a continuous plurality of intermediate rotated positions between the first fully rotated position and second fully rotated position, with the first fully rotated position and second fully rotated position separated by 180 degrees of rotation or less; and
stopping the cable guide from rotating beyond the first fully rotated position or second fully rotated position.

15. The method of claim 14, wherein rotating the cable guide relative to the C-arm includes rotating the cable guide around a rotational axis arranged at an angle to a mounting surface of the C-arm, the cable guide rotatably coupled to the C-arm at the mounting surface.

16. The method of claim 14, wherein coupling the cable guide around the cable includes enclosing a portion of the cable between a first section and a second section of a rigid elongate portion of the cable guide.

17. The method of claim 14, wherein rotating the cable guide relative to the C-arm includes rotating the cable guide via gravity and without driving the cable guide by motor.

* * * * *